(12) United States Patent
Diamond

(10) Patent No.: US 7,662,629 B2
(45) Date of Patent: *Feb. 16, 2010

(54) PEPTIDE SCAFFOLDS FOR TRANSFER OF MOLECULES INTO EUKARYOTIC CELLS

(75) Inventor: Scott L. Diamond, Bala Cynwyd, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 18 days.

This patent is subject to a terminal disclaimer.

(21) Appl. No.: 11/755,219

(22) Filed: May 30, 2007

(65) Prior Publication Data

US 2007/0231862 A1    Oct. 4, 2007

Related U.S. Application Data

(60) Division of application No. 11/058,988, filed on Feb. 16, 2005, now Pat. No. 7,244,704, which is a continuation of application No. 09/763,982, filed as application No. PCT/US99/20122 on Sep. 1, 1999, now Pat. No. 6,927,278.

(60) Provisional application No. 60/098,791, filed on Sep. 1, 1998.

(51) Int. Cl.
    C12N 15/00    (2006.01)
    C12N 5/00     (2006.01)
    C12P 21/06    (2006.01)
    A61K 38/04    (2006.01)

(52) U.S. Cl. .................. 435/455; 530/300; 530/350; 435/320.1; 435/69.1; 435/325

(58) Field of Classification Search .................. None
See application file for complete search history.

(56) References Cited

U.S. PATENT DOCUMENTS 5,661,025 A * 8/1997 Szoka et al. .............. 435/458
5,858,358 A * 1/1999 June et al. ................. 424/130.1
5,922,859 A * 7/1999 Birnstiel et al. ............ 536/24.5
6,927,278 B1 * 8/2005 Diamond .................... 530/300
7,244,704 B2 * 7/2007 Diamond ........................ 514/2

FOREIGN PATENT DOCUMENTS

WO    WO 92/13570    *  8/1992
WO    WO 96 41606       12/1996
WO    WO 96/41606    * 12/1996

OTHER PUBLICATIONS

Grondin et al (J. Biol. Chem. 271(26): 15458-15467, 1996).*
Sachdev et al (Mol. Cell. Biol. 18(5): 2524-2534, 1998).*
Fan et al (PNAS 95: 15293-15298, 1998).*
Jakel et al (EMBO Journal, (May 4, 1999) 18 (9) 2411-23).*
Gorlich (Journal of Cell Biology, (Jul. 14, 1997) 138 (1) 65-80).*
Michael et al (EMBO J. 16(12): 3587-3598, 1997).*
Michael et al (Cell 82(3): 415-422, 1995).*
GenBank Accession I39311.*
GenBank Accession 1K5J_E.*
Jans et al (Medicinal Research Reviews (1998) 18(4): 189-224).*
Jans et al., "Signals Mediating Nuclear Targeting and Their Regulation: Application in Drug Delivery", *Medicinal Research Reviews* 1998 18:4 189-223.
Chan et al., "Mutual exclusivity of DNA binding and nuclear localization signal recognition by the yeast transcription factor GAL4:implications for nonviral DNA delivery" *Gene Therapy* 1998 5:1204-1212.
Shen W-C., "Nuclear import of DNA:the ultimate targeting in gene therapy", *Journal of Drug Targeting* 1997 5(1): 11-13.

* cited by examiner

*Primary Examiner*—Richard Schnizer
(74) *Attorney, Agent, or Firm*—Licata & Tyrell P.C.

(57) ABSTRACT

Compositions and methods of using compositions with a nuclear targeting peptide containing a nonclassical nuclear localization signal to deliver selected molecules to the nucleus of eukaryotic cells are provided. The compositions are particularly useful in gene transfer methods.

6 Claims, 4 Drawing Sheets

SEQUENCE LISTING

<160> NUMBER OF SEQ ID NOS: 19

<210> SEQ ID NO 1
<211> LENGTH: 42
<212> TYPE: PRT
<213> ORGANISM: Artificial Sequence
<220> FEATURE:
<223> OTHER INFORMATION: Synthetic peptide

<400> SEQUENCE: 1

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

-continued

Arg Asn Gln Gly Gly Tyr Gly Gly Gly Cys
        35                  40

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide

<400> SEQUENCE: 2

Val Lys Lys Gly Lys Cys Arg Pro Gly Lys Gly Tyr Gly
1               5                   10

<210> SEQ ID NO 3
<211> LENGTH: 38
<212> TYPE: PRT
<213> ORGANISM: Artificial Sequence
<220> FEATURE:
<223> OTHER INFORMATION: Synthetic peptide

<400> SEQUENCE: 3

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 4
<211> LENGTH: 39
<212> TYPE: PRT
<213> ORGANISM: Artificial Sequence
<220> FEATURE:
<223> OTHER INFORMATION: Synthetic peptide

<400> SEQUENCE: 4

Tyr Asp Arg Arg Gly Arg Pro Gly Asp Arg Tyr Asp Gly Met Val Gly
1               5                   10                  15

Phe Ser Ala Asp Glu Thr Trp Asp Ser Ala Ile Asp Thr Trp Ser Pro
            20                  25                  30

Ser Glu Trp Gln Met Ala Tyr
        35

<210> SEQ ID NO 5
<211> LENGTH: 13
<212> TYPE: PRT
<213> ORGANISM: Artificial Sequence
<220> FEATURE:
<223> OTHER INFORMATION: Synthetic peptide

<400> SEQUENCE: 5

Cys Gly Tyr Gly Pro Lys Lys Lys Arg Lys Val Gly Gly
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Pro Pro Lys Lys Lys Arg Lys Val
1               5

```
<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Ser Cys Lys Arg Pro Arg Pro
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide

<400> SEQUENCE: 8

Ser Val Thr Lys Lys Arg Lys Leu
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide

<400> SEQUENCE: 9

Pro Pro Lys Lys Ala Arg Glu Asp
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Val Ser Arg Lys Arg Pro Arg Pro
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Pro Ala Ala Lys Arg Val Lys Leu
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Arg Lys Thr Lys Lys Lys Ile Lys
1               5
```

```
<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Ile Arg Lys Asp Arg Arg Gly
1               5

<210> SEQ ID NO 14
<211> LENGTH: 20
<212> TYPE: PRT
<213> ORGANISM: Artificial Sequence
<220> FEATURE:
<223> OTHER INFORMATION: Synthetic peptide

<400> SEQUENCE: 14

Ala Val Lys Arg Pro Ala Ala Thr Lys Lys Ala Gly Gln Ala Lys Lys
1               5                   10                  15

Lys Lys Leu Asp
            20

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide

<400> SEQUENCE: 15

Thr Arg Gln Ala Arg Arg Asn Arg Arg Arg Arg Trp Arg Glu Arg Gln
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide

<400> SEQUENCE: 16

Ala Leu Gly Ile Ser Tyr Gly Arg Lys Lys Arg Arg Gln Arg Arg Pro
1               5                   10                  15

<210> SEQ ID NO 17
<211> LENGTH: 18
<212> TYPE: PRT
<213> ORGANISM: Artificial Sequence
<220> FEATURE:
<223> OTHER INFORMATION: Synthetic peptide

<400> SEQUENCE: 17

Met Asp Ala Gln Thr Arg Arg Arg Glu Arg Arg Ala Glu Lys Gln Ala
1               5                   10                  15

Gln Trp

<210> SEQ ID NO 18
<211> LENGTH: 18
<212> TYPE: PRT
<213> ORGANISM: Artificial Sequence
<220> FEATURE:
<223> OTHER INFORMATION: Synthetic peptide

<400> SEQUENCE: 18
```

```
Gly Thr Ala Lys Ser Arg Tyr Lys Ala Arg Arg Ala Glu Leu Ile Ala
1               5                   10                  15

Glu Arg

<210> SEQ ID NO 19
<211> LENGTH: 4
<212> TYPE: PRT
<213> ORGANISM: Artificial Sequence
<220> FEATURE:
<223> OTHER INFORMATION: Synthetic peptide

<400> SEQUENCE: 19

Gly Gly Gly Cys
1
```

PEPTIDE SCAFFOLDS FOR TRANSFER OF MOLECULES INTO EUKARYOTIC CELLS

This application is a division of U.S. Ser. No. 11/058,983 filed Feb. 16, 2005, now U.S. Pat. No. 7,244,704, which is a continuation of U.S. Ser. No. 09/763,982 filed Apr. 25, 2001, now U.S. Pat. No. 6,927,278, which is the U.S. National phase of PCT/US1999/020122 filed Sep. 1, 1999; which claims priority to U.S. Ser. No. 60/098,791 filed Sep. 1, 1998, each of which are herein incorporated by reference in their entireties.

FIELD OF THE INVENTION

The present invention relates to peptide based compounds that overcome the final rate limiting step of nuclear entry encountered during lipofection of plasmids to nondividing cells thereby increasing the efficiency of nonviral gene transfer methodologies (i.e. lipofection). The present invention also relates to methodologies for delivering plasmids into the nucleus of mammalian cells, including nondividing mammalian cells via these peptide based compounds. The compounds and methods of the present invention rely upon nuclear targeting peptides (NTPs) comprising nonclassical nuclear localization signals of eukaryotic cells such as mammalian cells to exploit endogenous import and export mechanisms of ribonucleic acid trafficking to transfer selected molecules including genes to the nucleus of the cells. An example of an NTP useful in the present invention is the M9 sequence of the heteronuclear ribonuclear protein type 1 (hnRNP A1). One embodiment of the present invention involves the chemical conjugation of a small cationic peptide with known DNA complexing/compacting activity, termed the scaffold, to an NTP with an engineered carboxy terminal cysteine residue which facilitates conjugation. As demonstrated herein, compositions comprising an NTP containing a nonclassical nuclear localization signal or scaffold-NTP conjugates of the present invention are highly efficient in transfecting nondividing mammalian cells with selected molecules.

BACKGROUND OF THE INVENTION

Gene transfer by nonviral methodologies (i.e. lipofection) has been found to be very inefficient in nondividing cell populations. Unfortunately, cells are not actively dividing in many in vivo tissues that are potential clinical targets for gene therapy. While receptor targeting, fusigenic peptides, or endosome disrupting agents help overcome some of the first barriers that limit liposome-based gene delivery, thus far virus free gene transfer using liposomes has had limited clinical utility because of the difficulty of transporting genetic material into the nucleus of a nondividing cell.

Cationic liposomes are commonly used as a means of delivering DNA to dividing cells in culture. DNA/lipid aggregates form spontaneously after mixing aliquots of the liposome reagent with an aqueous solution of DNA (Felgner et al. *Proc. Natl Acad. Sci.* U.S.A. 1987 84, 7413; Felgner et al. *J. Biol. Chem.* 1994 269, 2550; Felgner, P. L. and Ringold, G. M. *Nature* 1989 337, 387). However, the efficiency of transfection is low with nondividing cells and certain target cells such as endothelium. For example, COS-7 cells lipofected with chloramphenicol acetyl transferase (CAT) gene are nearly 80% CAT positive compared to essentially no CAT expression in endothelial cells (Nathwani et al. *Brit. J. Haem.* 1994 88, 121).

Arterial gene transfer has been proposed for the treatment of atherosclerosis and restenosis following angioplasty. The two major strategies of arterial gene transfer are: (1) the cultivation, transfection and reintroduction of autologous endothelial cells to the recipient, (Dichek et al. *Circulation* 80, 1347, 1989; Wilson et al. *Science.* 244, 1344, 1989) and (2) the direct catheter delivery of genetic material with transfection vehicle or virus to the cells of the artery (Nabel et al. *Science* 244, 1342, 1989; Lemarchand et al. *Proc. Natl Acad. Sci.* 89, 6482, 1992; Flugelman et al. *Circulation.* 85, 1110, 1992; Takeshita et al. *J. Clin. Invest.* 93, 652, 1994; Nabel E. G., *J. Vasc. Sur.,* 15, 931, 1992; Chapman et al. *Circ. Res.* 71, 27, 1992; Schulick et al. *Circ. Res.* 77, 475, 1995). While receptor targeting of vectors to endothelium may provide benefit, the endothelium is ideally accessible by catheter. In vivo, endothelial cells have a very low mitotic rate. Hence, while adenoviral gene transfer (Flugelman et al. *Circ.* 1992 85:1110-1117; Nabel et al. *Science* 1989 244:1342-1344; Subramanian, A. and Diamond, S. L. *Tissue Engineering* 1997 3:39-52; Lemarchand et al. *Circ. Res.* 1993 72:1132-1138; Steg at al. *Circ.* 90:1648-1653; Sung et al. *Circ. Res.* 1993 73:797-807; Schachtner et al. *Circ. Res.* 1995 76:701-709) is highly efficient in transfecting these cells, gene transfer via liposome mediated routes and retroviral vectors which are more efficient in mitotic cells (Flugelman et al. *Circulation.* 85, 1110, 1992 1992) result in low levels of gene transfer.

Thus, various attempts have been made to improve efficiency of gene transfer of nondividing cells via liposome mediated routes.

Recent improvements of lipofection protocols for subconfluent epithelium tend to plateau at about 30% transfection efficiency: $\beta_5\beta_1$ integrin targeting peptide results in 25% transfection of corneal endothelium (Hart et al. *Hum. Gene Ther.* 1998 9:575-585); replication-deficient AdV-complexed plasmid results in 20% transfection of HUVEC (Edgell et al. *Biotechniques* 1998 25:264-268) and 25 to 35% transfection of BAEC (Go et al. *Am. J. Physiol.* 1998 274:H1-H7); histone complexation of plasmid results in 20% transfection of bovine aortic endothelial cells (BAEC) (Subramanian, A. and Diamond, S. L. *Tissue Engineering* 1997 3:39-52); AdV fiber added to plasmid results in 30% transfection of BAEC (Hong et al. *Chin. Med. J.* 1995 108:332-338) and plasmid condensed with recombinant histone H1 containing SV40 T-antigen NLS resulted in 10 to 30% transfection of COS-7 or NIH3T3 (Fritz et al. *Hum Gene Ther.* 1996 7:1395-1404). It is not known whether the benefits of these protocols can be achieved when using confluent cells at the time of transfection. The 30% plateau is believed to represent the persistence and elevated level of intact cytoplasmic plasmid available to accomplish gene transfer in cells dividing at times one to two days after transfection. An unprotected plasmid with short half-life in the cytoplasm would transfect only the cells dividing in the first few hours after the lipofection.

A large amount of labeled-plasmid transfected into the cells via these protocols was found to be present in the endosomes as indicated by punctate staining. However when the plasmids were transcribed cytoplasmically using a T7 RNA polymerase based system, 80% of cells were found to express $\beta$-galactosidase, indicating that some of the plasmid does get out of the endosome into the cytoplasm in the cells.

However, plasmid DNA cannot readily enter the nucleus since they are typically excluded by the nuclear pore (Felgner et al. *Proc. Natl Acad. Sci. USA* 1987 84:7413-7417; Felgner, P. L. and Ringold, G. M. *Nature* 1987 337:387-388; Jo et al. *J. Biol. Chem.* 1997 272:1395-1401; and Zabner et al. *J. Biol. Chem.* 1995 270:189997-19007). Increasing cytoplasmic concentrations of plasmid can directly enhance total expression in dividing cells by enhancing plasmid levels in the nucleus, post-mitotically. It is believed that the frequency of nuclear import events in nondividing cells increases with elevated plasmid levels through enhancement of the probability of plasmid encounter with the nuclear pore entrance. However, inefficient nuclear pore targeting due to cytoplasmic sequestration (scaffolding) and inefficient transit of plasmid across the pore remain important rate limits during nonviral gene transfer.

Attempts to conjugate classical nuclear localization signals (NLS) to a plasmid to alleviate this problem have had limited success (Subramanian, A. and Diamond, S. L. *Tissue Engineering* 1997 3:39-52; Fritz et al. *Hum. Gene Ther.* 1996 7:1395-1404). Classical nuclear localization signals involve peptide sequences of clustered residues that interact with two proteins, importin-þ and importin-þ, also known as karyopherin þand karyopherin þ, respectively. The protein importin-þ binds the nuclear pore. The importin complex also binds a GTPase RNA (Nakielny et al. *Exp. Cell Res.* 1996 229:261-266). Examples of classical NLS include SV40 large T antigen (PPKKKRKV; SEQ ID NO:6), adenovirus E1A (SCKRPRP; SEQ ID NO:7), human lamin A (SVTKKRKL; SEQ ID NO:8); polyoma large T antigen (PPKKARED; SEQ ID NO:9), polyoma large T antigen (VSRKRPRP; SEQ ID NO:10), human c-myc (PAAKRVKL; SEQ ID NO:11), rat glucocorticoid receptor (RKTKKKIK; SEQ ID NO:12), and human estrogen receptor (IRKDRRG; SEQ ID NO:13). The classical nuclear localization sequence can also contain a bipartite form, with two basic amino acids separated by an amino acid spacer from a second cluster of three or more basic amino acids. A prototypical bipartite NLS is found in nucleoplasmin (AVKRPAATKKAGQAKKKKLD; SEQ ID NO:14).

It has been found that histones (Subramanian, A. and Diamond, S. L. *Tissue Engineering* 1997 3:39-52; Fritz et al. *Hum. Gene Ther.* 1996 7:1395-1404) or SV40 T antigen (Sebestyen et al. *Nature Biotech.* 1998 16:80-85) when linked covalently or by charge interactions to plasmid have not been able to get plasmid across the nuclear pore of intact cells to effect fully efficient gene transfer with 100% transfection.

In the present invention methods and compositions are providing for delivering selected molecules to the nuclei of eukaryotic cells via nuclear targeting peptides containing nonclassical nuclear localization signals.

SUMMARY OF THE INVENTION

An object of the present invention is to provide methods and compositions for delivering selected molecules to the nucleus of eukaryotic cells via targeting of nonclassical nuclear import pathways. In one embodiment, compositions comprising a nuclear targeting peptide containing a nonclassical nuclear localization signal which interacts with transportin are used to mediate nuclear pore targeting and import of molecules into the nucleus of the cells. By "selected molecule" it is meant to include, but is not limited to, organic molecules, polymers, proteins and nucleic acids useful for either therapeutic or research purposes.

Another object of the present invention is to provide a compound comprising a cationic peptide scaffold and a nuclear targeting peptide conjugated to the cationic scaffold via a hydrolytic resistant linkage. This compound is referred to herein as a Scaffold-NTP conjugate.

Another object of the present invention is to provide compositions suitable for lipofection of mammalian cells with a selected nucleic acid sequence which comprise a selected nucleic acid sequence, a peptide scaffold and an NTP. In a preferred embodiment, a complex is formed between a plasmid containing the selected nucleic acid sequence and a Scaffold-NTP conjugate.

Another object of the present invention to provide a method for expressing a selected nucleic acid sequence in mammalian cells which comprises contacting cells with a mixture of a selected nucleic acid sequence, a peptide scaffold and an NTP.

Another object of the present invention is to provide a method for expressing a selected nucleic acid sequence in mammalian cells which comprises forming a complex between a plasmid containing the selected nucleic acid sequence and a scaffold-NTP conjugate; and contacting cells with the complex.

Another object of the present invention is to provide cells transfected with a complex comprising a plasmid containing a selected nucleic acid sequence and a scaffold-NTP conjugate.

Yet another object of the present invention is to provide a method of treating a patient suffering from a condition associated with an absence in the expression of a normal selected nucleic acid sequence comprising administering to the patient a composition comprising a complex formed between a plasmid containing the selected nucleic acid sequence and a Scaffold-NTP conjugate.

BRIEF DESCRIPTION OF THE DRAWINGS

FIG. 2 provides results from experiments demonstrating lipofection of confluent BAEC with pCMVþgal in the presence and absence of peptides.

DETAILED DESCRIPTION OF THE INVENTION

Figure 1:
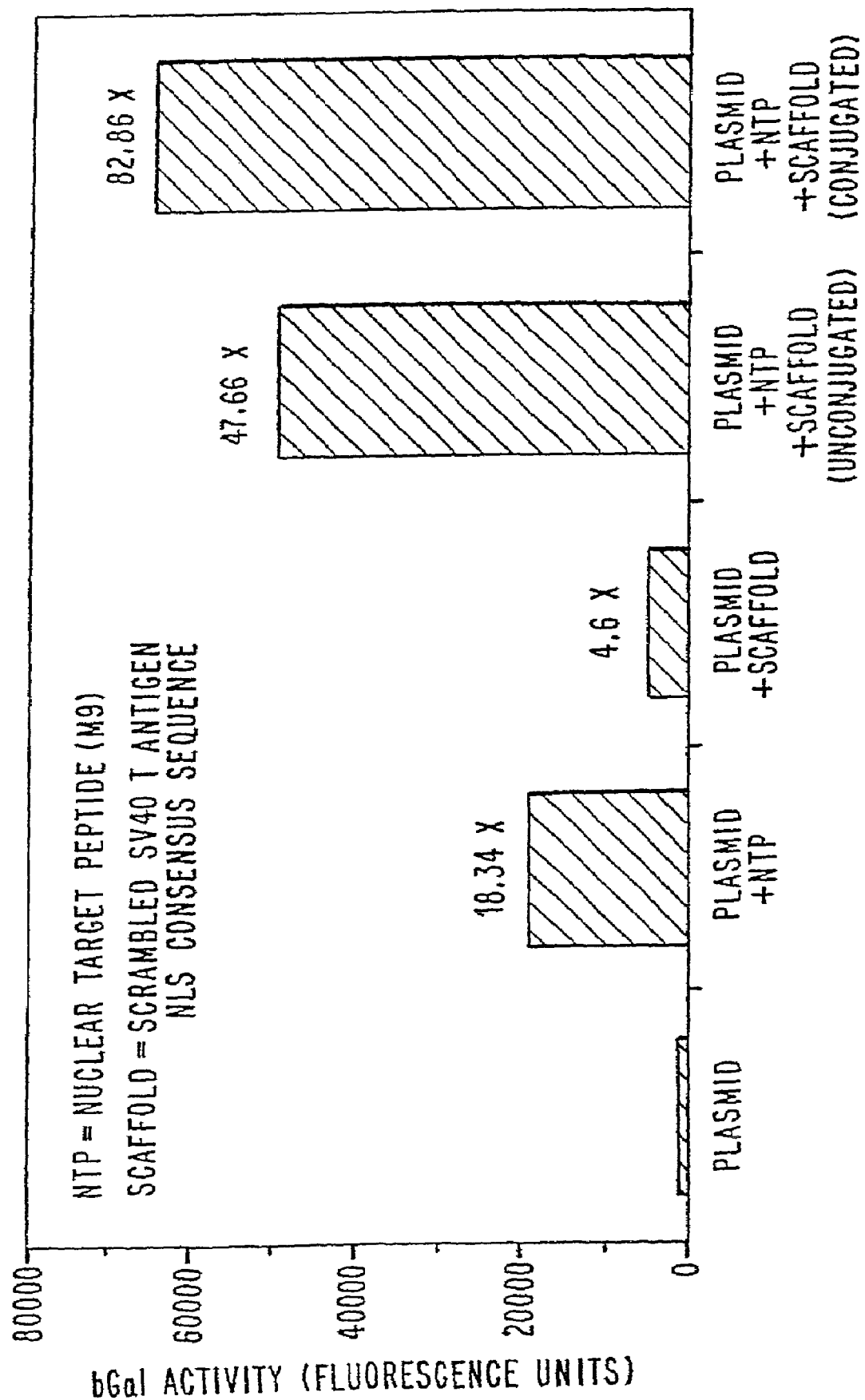
FIG. 1 is a bargraph showing the enhancement of total expression of þ-galactosidase activity following complexation of pCMVþgal with a nuclear targeting peptide containing the M9 sequence. In all samples, cells counts were kept at $10^7$ cells/ml.

The present invention relates to a new approach for high efficiency nonviral gene transfer across the nuclear pore by exploiting endogenous import and export mechanisms of ribonucleic acid trafficking which utilize nuclear targeting peptides containing nonclassical nuclear localization signals. Peptide based compounds that overcome the final rate limiting step of nuclear entry encountered during lipofection of plasmids to nondividing cells have now been designed and demonstrated to be effective at transfecting mammalian cells, and in particular nondividing mammalian cells.

The compounds of the present invention comprise a nuclear targeting peptide, termed the NTP. The NTP comprises a peptide sequence containing a nonclassical, nuclear localization signal (NLS) of eukaryotic cells. Examples of nonclassical nuclear localization signals include, but are not limited to, M9 of hnRNP A1, KNS of hnRNP K, and HNS of HuR. In contrast to classical nuclear localization signals, these nonclassical NLS do not interact with proteins such as importin-α and importin-β. Instead, the nonclassical NLS of hnRNP A1, termed the M9 sequence, binds a 90 kDa intracellular protein called transportin which mediates nuclear pore targeting and import. The nonclassical NLS of HuR, termed the HNS, shows some homology with the M9 sequence. The nonclassical NLS of HnRNP K, termed the KNS, utilizes an import pathway independent of either the M9 or the classical NLS import pathway and has been suggested to interact directly with the nuclear pore (Michael et al. The *EMBO J.* 1997 16:2587-3598). In a preferred embodiment the NTP comprises the M9 sequence (NQSSNFGPMKGGNFG-GRSSGPYGGGGQYFAKPRNQGGY; SEQ ID NO:3) of the heteronuclear ribonuclear protein type 1 (hnRNP A1) protein or a similar NTP with the ability to interact with transportin to mediate nuclear pore targeting and import of selected molecules.

The M9 epitope of human hnRNP A1 is a small, potentially nonimmunogenic sequence with no homology with known fusigenic epitopes. This nonclassical, NLS is not highly cationic and does not display strong DNA binding properties. Thus, in one embodiment of the present invention, the M9 sequence is engineered with a carboxy terminal cysteine residue (NQSSNFGPMKGGNFGGRSSGPYGGGGQYFAKPRNQGGY-GGGC;

SEQ ID NO: 1)

to facilitate conjugation to a scaffold peptide to improve the DNA binding properties of the NTP. It is preferred that the NTP be conjugated to a small cationic peptide with known DNA complexing/compacting activity, termed the scaffold. Peptide sequences ranging in length from 5 to 200 amino acids and enriched in basic amino acid residues including lysine, arginine and histidine provide useful scaffolds. Also useful as scaffolds are peptide sequences containing the consensus sequence RNA-binding domain (CS-RBD) which is found in hnRNP A1. Examples of peptides capable of acting as scaffolds in the compounds of the present invention include, but are not limited to,

```
HIV rev    (TRQARRNRRRRWRERQ; SEQ ID NO:15),
HTV tat    (ALGISYGRKKRRQRRP; SEQ ID NO:16),
pN         (MDAQTRRRERRAEKQAQW; SEQ ID NO:17),
and
p21N       (GTAKSRYKARRAELIAER; SEQ ID NO:18).
```

A preferred scaffold sequence useful in the present invention comprises a scrambled SV40 T antigen (ST), also referred to herein as a mutant SV40 T antigen, which has five positively charged amino acids (VKKGKCRPGKGYG; SEQ ID NO:2).

The peptide scaffold and the NTP are preferably conjugated via a hydrolytic-resistant chemical linkage. In one embodiment, chemical conjugation of the peptide scaffold to the NTP is achieved using a crosslinker such as succinimidyl 4-(N-maleimidomethyl)cyclohexane-I (SMCC). However, other homobifunctional or heterobifunctional crosslinkers are well known and used routinely by those of skill in the art. For example, for conjugation of an NTP containing a terminal cysteine and a scaffold peptide containing a cysteine, the following homobifunctional linkers can be used in a two step reaction: sulfhydryl to sulfhydryl homobifunctional crosslinker: bis-maleimidoethane; bis-maleimidohexane; 1,4-bis-maleimidyl-2,3-dihydroxybutane; or 1,4-bis-maleimidobutane. For conjugation of an NTP containing a terminal cysteine and a scaffold peptide containing a terminal amine, the following heterobifunctional linkers can be used in a two step reaction: sulfhydryl to amino heterobifunctional crosslinker: N-succinimidyl[4-iodoacetyl]aminobenzoate; N-succinimidyl iodoacetate; succinimidyl 3-[bromoacetamido]propionate; succinimidyl 4-[p-maleimidophenyl]butyrate; succinimidyl-6-[(β-maleimidopropionamido)hexanoate]; N-succinimidyl 3-[2-pyridyldithio]propionate; N-[ɣ-maleimidobutyryloxy]sulfo-succinimide ester; N-[β-maleimidoundecanoyloxy]-sulfosuccinimide ester; m-maleimidobenzoyl-N-hydroxysulfosuccinimide ester; or N-succinimidyl-[4-vinylsulfonyl]benzoate.

Scaffold-NTP conjugates can also be prepared via recombinant expression through bacterial or eukaryotic expression systems of a protein containing a cationic charge and an NTP such as the M9 sequence. Bacterial and eukaryotic expression systems are well known and used routinely by those skilled in the art.

A Scaffold-NTP conjugate of the present invention, M9-ScT has been demonstrated to be highly efficient in transfecting confluent, nondividing large artery aortic mammalian endothelial cells.

In experiments lipofecting confluent bovine aortic endothelial cells with M9-ScT/rhodamine plasmid, the majority of fluorescence was endosomal indicating that the M9 sequence is not fusigenically active. When confluent bovine aortic endothelial cells (BAEC) were lipofected with rhodamine-plasmid for 16 hours, highly punctate staining was observed in the cytoplasm of every cell, demonstrating that endosomal compartmentalization of plasmid was sustained. Nuclear levels in these cells were extremely low in comparison. Highly confluent BAEC transfected for 20 hours with pTMβgal and T7 RNA polymerase to allow for cytoplasmic transcription of the plasmid resulted in nearly 80% of the cells expressing β-galactosidase. Without addition of the T7 RNA polymerase, the flow cytometry signal was due to the level of endogenous activity and FDG autofluorescence detected in untransfected cells. Endosome escape, though not efficient during lipofection, was widely detectable in the population of confluent BAEC. Xgal staining of confluent BAEC lipofected with pTMβgal/T7 RNA polymerase demonstrated that over half of the cells were intensely blue and the other half were moderately blue.

Figure 2A:
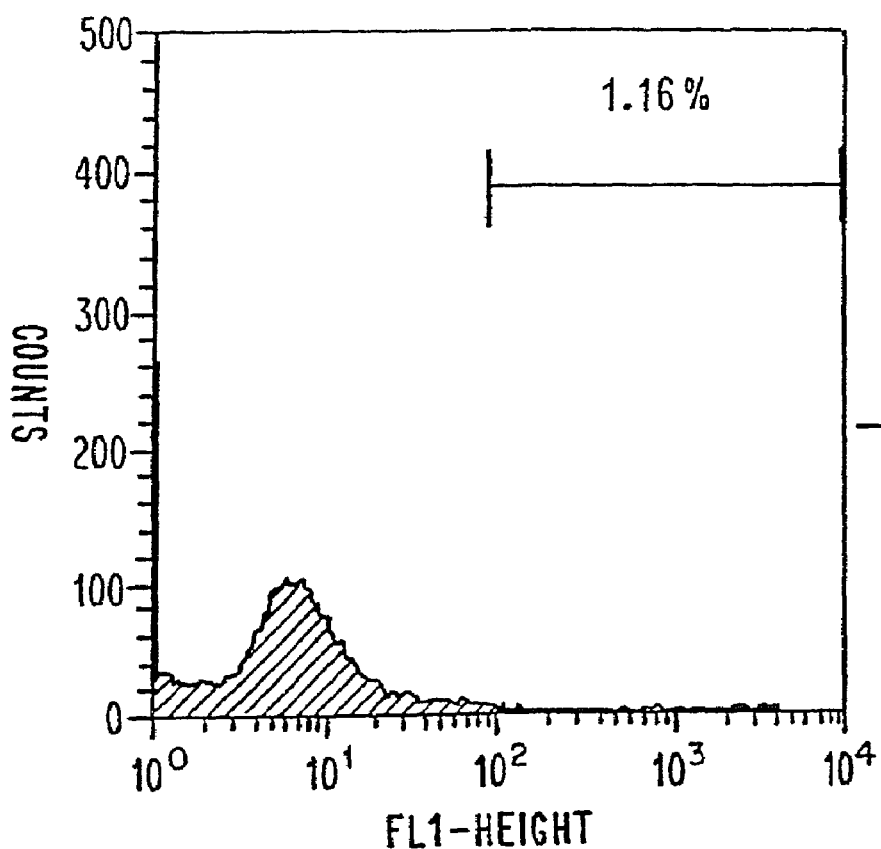
FIG. 2A shows the fluorescence of untransfected BAEC. These cells were used as a measure of endogenous galactosidase activity and FDG autofluorescence.
Figure 2B:
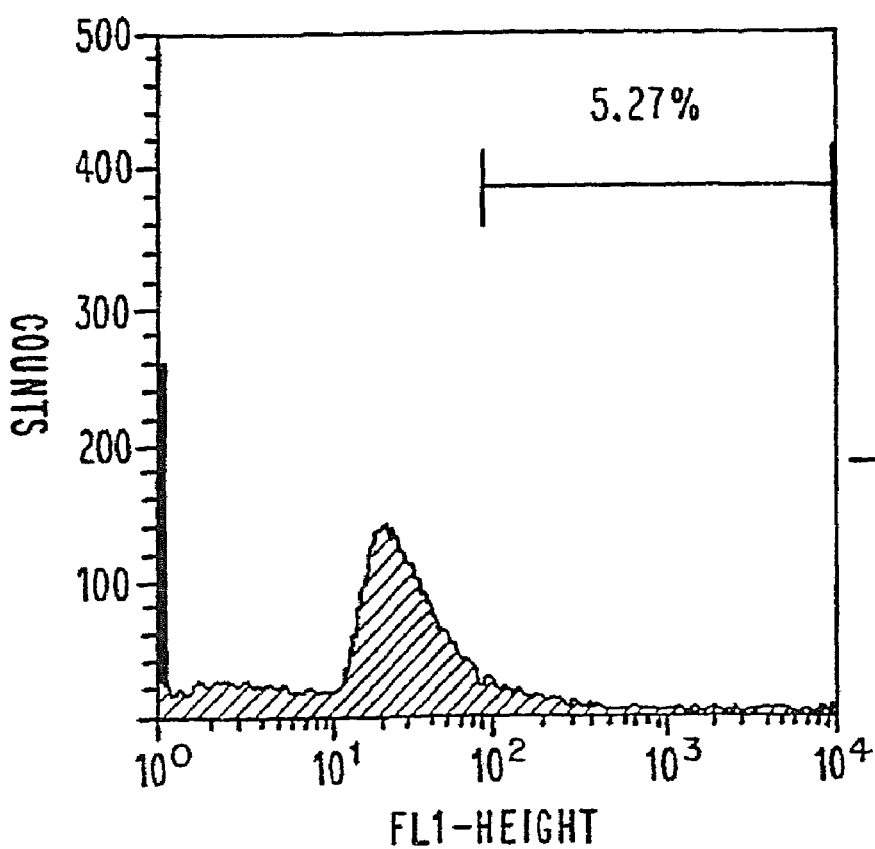
FIG. 2B shows the fluorescence of confluent BAEC transfected with 1 µg plasmid alone.
Figure 2C:
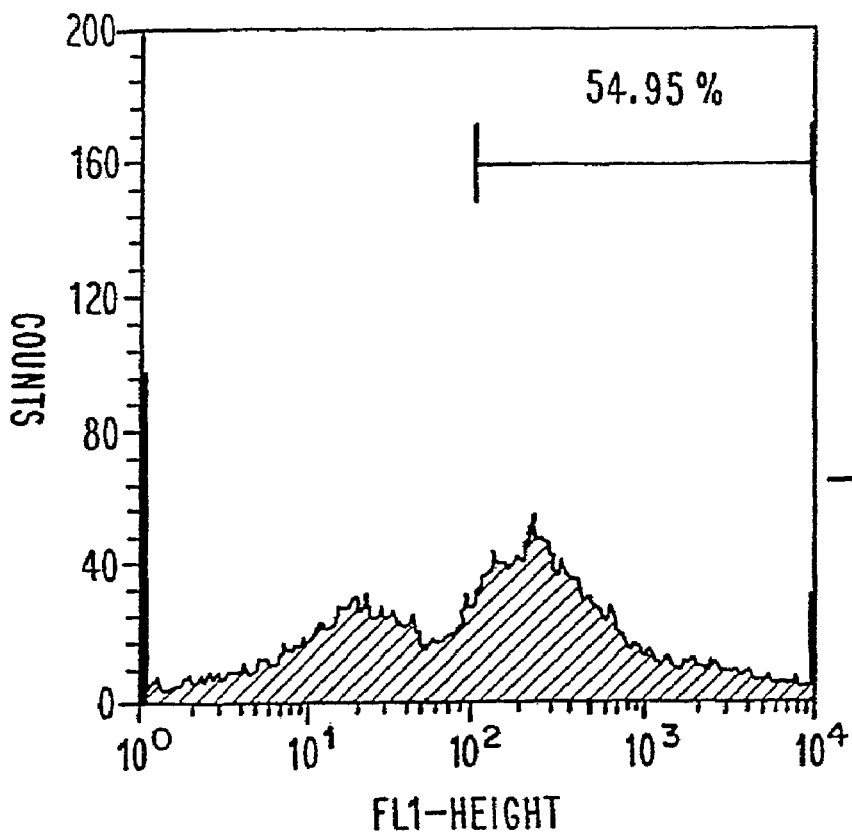
FIG. 2C shows the fluorescence of confluent BAEC transfected with 1 µg plasmid plus 60 µg of M9 peptide.
Figure 2D:
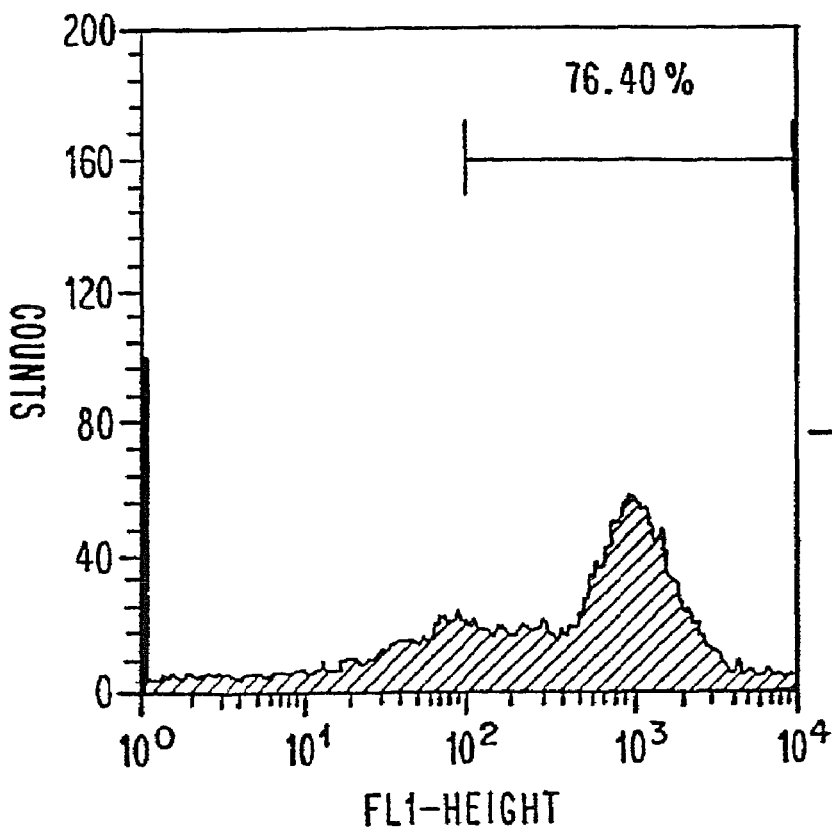
FIG. 2D shows the fluorescence of confluent BAEC transfected with 1 µg plasmid plus 30 µg of M9 plus 30 µg of ScT (unconjugated).
Figure 2E:
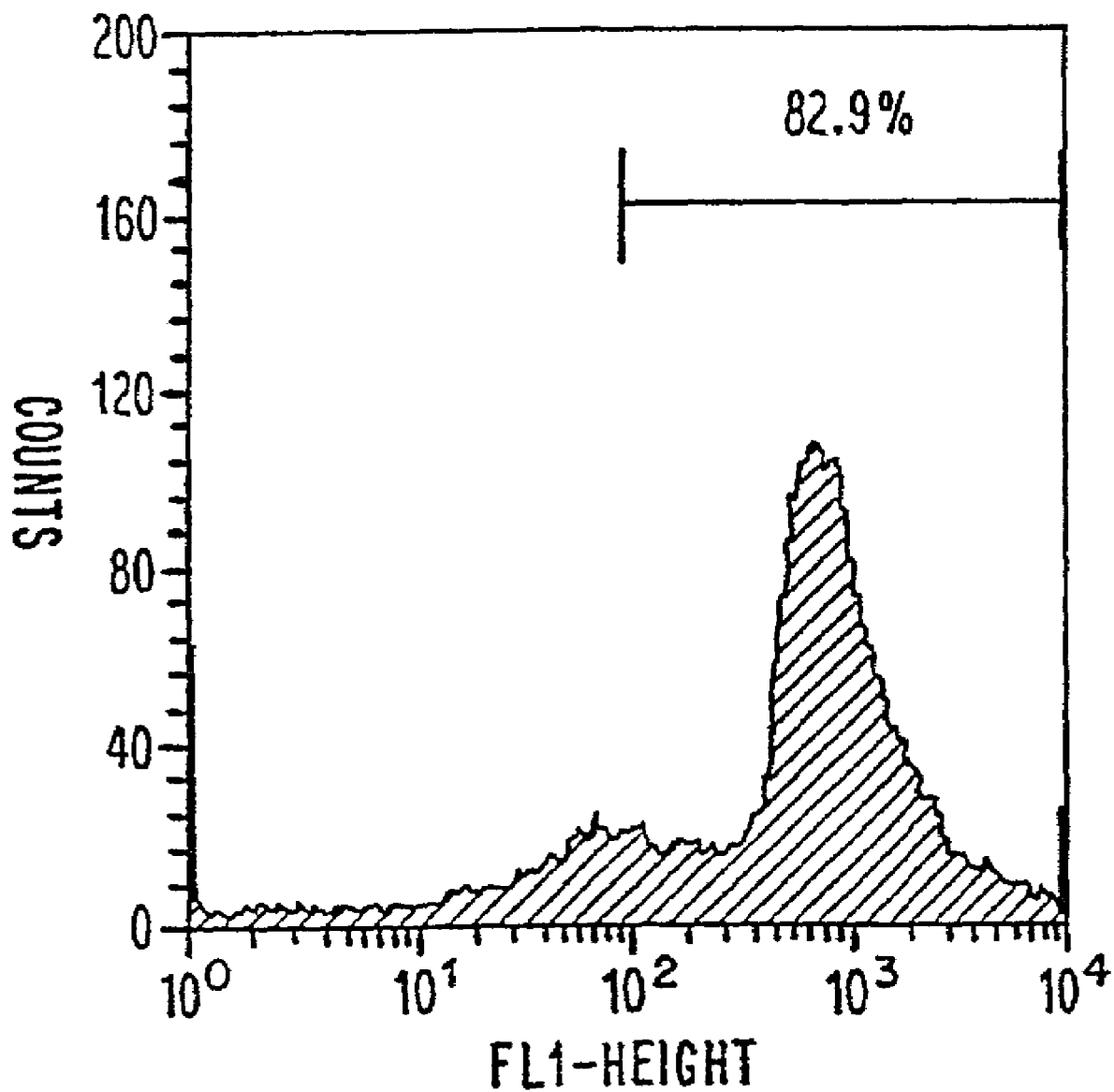
FIG. 2E shows the fluorescence of confluent BAEC transfected with 1 µg plasmid+60 µg M9-ScT conjugate. Percent transfection is defined in each panel by the percent of cells with ≧100 f.u.

Highly confluent BAEC monolayers transfected with plasmid alone resulted in about 1% of the cells staining Xgal positive for β-galactosidase. In contrast, nearly all the cells displayed Xgal staining to varying extent when lipofected with pCMVβgal complexed with the M9-ScT conjugate. Confluent BAEC were then lipofected with pCMVβgal complexed to various combinations of peptides and analyzed by flow cytometry (see FIG. 2A-E). The majority of untransfected cells had a fluorescence of <10 f.u. This low level of fluorescence was due to endogenous galactosidase activity and FDG autofluorescence (see FIG. 2A). When confluent BAEC were transfected with pCMVβgal alone (see FIG. 2B), the majority of cells displayed a signal above 10 f.u. demonstrating that lipofection provided for extremely low level, but widespread expression that is below the sensitivity of Xgal staining. Only 5.27% of cells lipofected with plasmid alone had fluorescence above 100 f.u. This level increased to 55% when the plasmid was precomplexed with M9 peptide alone (see FIG. 2C). Adding M9 and ScT to the plasmid without chemical conjugation resulted in a transfection efficiency of 76.4% (see FIG. 2D). This marked increase with M9 alone or M9+ST (unconjugated) was in the absence of the nonpeptide SMCC crosslinker. The highest transfection efficiency of 83% was obtained when confluent BAEC were lipofected with plasmid complexed with M9-ScT indicating that binding of M9 peptide to the cationic ScT peptide led to increased transfection efficiency (see FIG. 2E). In highly confluent monolayers of BAEC, the use of M9-ScT conjugate provided for a 15.7-fold increase in the percent positive cells with $\geq 10^2$ f.u. measured by flow cytometry compared to lipofection with plasmid alone.

The total β-galactosidase expression in the cells was measured fluorometrically (see FIG. 1). Complexation of plasmid with M9 peptide alone provided a 18.3-fold increase in expression. This increase was not simply due to a condensation effect since ScT which condenses plasmid effectively by electrostatic interactions (as observed by an ethidium bromide fluorescence release assay) provided only a 4-fold increase in β-galactosidase expression. A similar level of increase in β-galactosidase expression was observed when the plasmid was complexed with SV40 T-antigen consensus NLS or with polylysine (13 amino acid peptide), indicating that classical NLS (or sequences with equivalent charge density and size) were markedly less efficient in targeting the plasmid to the nucleus as compared to M9 NLS. Transfection of confluent BAEC with plasmid precomplexed with M9-ScT conjugate resulted in a 63-fold enhancement in expression over transfection with plasmid alone, while M9+ST (unconjugated) complexed to plasmid resulted in a 47-fold increase.

To investigate nuclear localization activity of M9-peptide, confluent BAEC were treated with digitonin to permeabilize the plasmalemma and then incubated with fluorescent plasmid±M9-ScT conjugate for 30 minutes. The cells incubated with plasmid alone displayed cytoplasmic and perinuclear staining but no nuclear staining. Nuclear import of the complex of plasmid+M9-ScT conjugate was not observed in cells pretreated with wheat germ agglutinin (WGA) to block nuclear pores. However, when cells were incubated with plasmid complexed with M9ScT, the amount of plasmid in the nucleus increase markedly.

Similarly, complexation of plasmid with a cationic peptide alone that aids in plasmid condensation and protection against DNases provided only a modest 4-fold enhancement in expression.

Thus, by flow cytometry, transfection of confluent mammalian cells with plasmid alone resulted in only 5% of the cells testing positive, while 76.4% of the cells were positive when a mixture of M9, ScT and plasmid were added to the cells without chemical conjugation and 83% of the cells were positive when the plasmid was complexed with the M9-ScT compound of the present invention. This compound, M9-ScT, caused a 60-fold increase in total β-galactosidase expression over transfection with plasmid alone. These striking differences were seen in replicate cultures of confluent cells with the same cell density at the time of transfection or at the time of assay. The role of enhanced nuclear import by this compound of the present invention is further supported by results from a nuclear import assay. Permeabilized BAEC cells incubated with plasmid labeled with rhodamine showed very distinct cytoplasmic and perinuclear staining but no staining in the nucleus. When rhodamine-plasmid was complexed with the M9-ScT conjugate, accumulation was observed in the nucleus. This accumulation was inhibited by preincubation of the cells with an agent which blocks nuclear pores.

Accordingly compositions of the present invention comprising a nuclear targeting peptide containing a nonclassical NLS are useful in gene transfection methods. In one embodiment, the NTP, preferably the M9 sequence, is simply mixed with a plasmid containing the selected nucleic acid sequence. In another embodiment, a peptide scaffold is also added to the mixture. Cells are then contacted with the mixture so that the plasmid and selected nucleic acid sequence are transfected into the cells and the selected nucleic acid sequence is expressed. More preferably, cells are contacted with a composition comprising a complex of a plasmid containing a selected nucleic acid sequence and a scaffold-NTP conjugate of the present invention under conditions in which the plasmid is transfected into the cells and the selected nucleic acid sequence is expressed. Compositions of the present invention are useful in transfecting any mammalian cells with a selected nucleic acid sequence. However, the compositions of the present invention are particularly useful in transfecting nondividing mammalian cells such as endothelial cells. The compositions of the present invention are useful in gene transfer methods used to treat patients suffering from conditions associated with an absence in the expression of a normal selected nucleic acid sequence. This condition can thus result from no expression of the nucleic acid sequence or expression of a mutated nucleic acid sequence. Compositions of the present invention are believed to particularly useful in arterial gene transfer methods used in the treatment of atherosclerosis and restenosis following angioplasty.

Targeting of nonclassical nuclear import pathways via the compositions and methods of the present invention can also be used to deliver other selected molecules to the nucleus of eukaryotic cells. In addition to selected nucleic acid sequences, by "selected molecule" it is also meant to include, but is not limited to, organic molecules, polymers, and proteins. In a preferred embodiment, compositions comprising a nuclear targeting peptide containing a nonclassical nuclear localization signal which interacts with transportin such as the M9 sequence are used to mediate nuclear pore targeting and import of molecules into the nucleus of the cells. Eukaryotic cells can be contacted with a mixture of these compositions and a selected molecule to mediate nuclear pore targeting and import of the selected molecules into the nucleus of the cells.

The following nonlimiting examples are provided to further illustrate the present invention.

EXAMPLES

Example 1

Cell Culture

Bovine aortic endothelial cells (BAEC) (passage<10) are grown to confluence, passed to a 6-well culture dish at a split ratio of 1:3, and then grown to confluence as described by Subramanian, A. and Diamond, S. L. *Tissue Engineering* 3, 39-52, 1997. Growth medium is Dulbecco's modified Eagle's medium (DMEM) containing 10% heat inactivated newborn calf serum, 0.30 mg/ml of glutamine, 150 U/ml penicillin and 0.15 mg/ml streptomycin (GIBCO, Grand Island, N.Y.). Hela cells (Hela S3 ATCC No. CCL 2.2) are grown in DMEM media (Gibco BRL) supplemented with 10% fetal calf serum as described by Ranjan, V. and Diamond, S. L. *Biochem. Biophys. Res. Comm.* 196, 79, 1993.

Example 2

Transfection Procedure

Cationic liposomes (Lipofectamine Reagent, Gibco-BRL), containing a 3:1 by weight mixture of polycationic lipid 2,3-dioleoyloxy-N-[2(sperminecarboxamido)ethyl]-N,N-dimethyl-1 propanaminium trifluoroacetate (DOSPA) and the neutral lipid dioleoyl phosphatidylethanolamine (DOPE) was used in all transfections in accordance with procedures described by Subramanian, A. and Diamond, S. L. *Tissue Engineering* 3, 39-52, 1997. Pure liposome (10 μl) diluted to 100 μl are added to the DNA/scaffold complex, incubated for 45 minutes. Then 0.8 ml of OPTIMEM media is added to this mixture which is then overlaid on the cells. The cells are incubated for 2 hours at 37 °C. After two hours, the mixture is aspirated, 4% serum in OPTIMEM media is added, and the cells are allowed to grow for 48 hours. The cells are then fixed and assayed for β-gal activity. During the transfections, the cells are continuously monitored for cell viability and adhesion.

Example 3

βgal Assays—% Transfection, Total Expression and Flow Cytometry

To assay for βgal to measure % transfection, cells are stained with XGAL as described by Subramanian, A. and Diamond, S. L. *Tissue Engineering* 3, 39-52, 1997. The percent of cells stained per field of view is counted using a Zeiss 125M inverted microscope. The count is averaged from at least 4 fields of view for each transfected monolayer. To measure β-gal expression quantitatively, cell lysates are prepared and tested for β-gal activity against the fluorogenic substrate, fluorescein di-β-D-galactopyranoside (FDG, F-1179 Molecular Probes) which is not fluorescent until cleaved to fluorescein monogalactoside and then to fluorescein (excitation/emission: 494/520 nM). For flow cytometry, the trypsinized cell suspension is supplemented with serum, pelleted (100 g) and resuspended in staining medium to approximately $10^7$ cells/ml. A 100 μL cell suspension is maintained at 37 °C and 100 μl of 2 mM FDG maintained at 37 °C is then added to the cell suspension, mixed rapidly and incubated at 37 °C for 1 minute. The FDG loading is stopped at the end of 1 minute by adding 1.8 mL of ice-cold staining medium containing 1.5 μM Propidium Iodide and 1 mM PETG. The cells are kept on ice prior to flow cytometer analysis using a Becton Dickinson FACScan system. Unstained BAEC cells allow compensation for autofluorescence. The histogram showing fluorescence/cell to the number of cells is used to calculate the % transfection.

Example 4

Domains for Nuclear Targeting

The M9 sequence of hnRNP A1 is a 38 amino acid sequence that provides for import/export of a fusion β-gal-9 marker. The deletion of 5 amino acids from the carboxy or amino terminus abolishes its targeting activity (Michael et al. *Cell* 83, 415-422, 1995). The M9 sequence is:

(SEQ ID NO:3)
NQSSNFGPMKGGNFGGRSSGPYGGGGQYFAKPRNQGGY

For purposes of chemical conjugation, the M9 sequence has been synthesized with a carboxy terminus addition of Gly-Gly-Gly-Cys to give an accessible thiol group provided by the cysteine:

Nuclear Targeting Peptide (NPS)=

(SEQ ID NO:1)
NQSSNFGPMKGGNFGGRSSGPYGGGGQYFAKPRNQGGY-GGGC

The K nuclear shuttling domain (KNS) of the hnRNP K protein is a 39 amino acid sequence:

(SEQ ID NO:4)
YDRRGRPGDRYDGMVGFSADETWDSAIDTWSPSEWQMAY

Example 5

Chemical Conjugation of Nuclear Targeting Epitopes to Cationic Scaffolds

Several different cationic scaffolds that are rich in amine suitable for conjugation reactions and which mediate electrostatic complexation or condensation with plasmid are used. These scaffolds can include: SV40 T antigen NLS (SVT=CGYGPKKKRKVGG (SEQ ID NO:5)), a mutated version of the SV40 T antigen NLS (muT=VKKGKCRPGKGYG (SEQ ID NO:2)), poly-L-lysine (MW 1, 4, and 30-70 kDa), histone H1, and hydrophilic amine-terminated dendrimers (87,340 MW) of small size (8.4 nm) available through Polysciences, Inc. (Warrington, Pa.). These scaffolds are tested for DNA condensation using a fluorescence quench assay of ethidium bromide labeled plasmid. Synthetic peptides with a C-terminus Gly-Gly-Gly-Cys-COOH (SEQ ID NO:19) linked to M9 or KNS are grafted at 1:1 to 3:1 to the activated amine-rich scaffolds. The crosslinker succinimidyl 4-(N-maleimidomethyl)cyclohexane-1 (SMCC, Pierce) is added at a final concentration of 10 mM (at 10% DMSO) to 100 μg amine rich scaffold (pH 7.2, 25 °C for 2 hours) to react the SMCC NHS-ester to the primary amine of the scaffold. Excess SMCC and DMSO are removed by sephadex G-15 chromatography. The activated scaffold is conjugated with equimolar or 2 to 3-fold excess of the KNS or M9 peptide at 4 μC (16 hours) by maleimide reaction with the SH moiety of the C-terminal cysteine. Individual reaction species are isolated by electroelution or FLPC. Precipitation with this method has not been observed.

Example 6

NTP Containing M9 Sequence and Scaffold Containing a Mutated Sequence of SV40 T Antigen NLS in Confluent BAEC A nuclear targeting peptide (NTP) of M9-GGC (approximately 4.5 kDa) was chemically synthesized and then crosslinked using SMCC to activate the primary amine on a scrambled sequence containing the amino acids of the SV40 T-antigen NLS (Scaffold: 13 amino acids; MW approximately 1.5 kDa). The Scaffold-NTP conjugate was about 6 kDa. Addition of conjugated Scaffold-NTP provided marked benefit to transfection of growth-arrested confluent bovine aortic endothelium. Without addition of the crosslinking agent SMCC, the scaffold and the NTP remain as individual peptides and addition of these two peptides provided little enhancement of gene transfection of BAEC. The overall expression of the marker protein β-galactosidase was enhanced over 30-fold with the addition of Scaffold-NTP to plasmid prior to mixture with the lipofection vehicle of lipofectamine. The scaffold alone provided little benefit to gene transfer.

Example 7

Nuclear Import Assay

The nuclear import assay was conducted in accordance with procedures described by Adam and Gerace (*Meth. Enzy.* 1992 219:97-111). BAEC cells were washed in ice cold import buffer [20 mM Hepes (pH 7.3), 110 mM $KC_2H_3O_2$, 5 mM $NaC_2H_3O_2$, 2 mM $MgC_2H_3O_2$, 0.5 mM ethylene glycol-bis(þ-aminoethyl ether) N,N,N',N',-tetraacetic acid (EGTA), 2 mM DL-dithiothreitol (DTT) and 1 µg/ml each of aprotinin, leupeptin and pepstatin). The cells were permeabilized by incubation of cells with import buffer containing 40 µg/ml digitonin for 5 minutes and then washed with import buffer. A total of 10 µl of rhodamine labeled plasmid (0.1 µg/ml) was mixed with 40 µl complete import buffer [50%(v/v) rabbit reticulosate (Promega Corp.), 20 mM Hepes (pH 7.3), 11 mM $KC_2H_3O_2$, 5 mM $NaC_2H_3O_2$, 2 mM $MgC_2H_3O_2$, 0.5 mM EGTA, 2 mM DTT, 1 µg/ml each of aprotinin, leupeptin and pepstatin, 5 mM ATP, 5 mM creatinine phosphate, 20 U/ml creatinine phosphokinase). Cells were incubated at 30 þC for 30 minutes with a solution containing 10 µl of rhodamine-plasmid (0.1 µg/µl)±5 µl of M9 ScT conjugate (12 µg/µl), and 35 µl of complete import buffer. In import inhibition experiments, cells were preincubated with wheat germ agglutinin (WGA, 40 µg/ml) in import buffer for 20 minutes prior to adding rhodamine-plasmid±peptide. The coverslips were rinsed with import buffer, mounted on a slide, and then observed by phase contrast and epifluorescence microscopy using an inverted Zeiss Axiophot microscope equipped with a 63X planapo (NA 1.4) lens.

Example 8

Delivery of NTP or NTP-Scaffold with Plasmid to Cells in Culture

An NTP containing the M9 sequence or other nonclassical NLS (from 0.001 µg to 100 µg NTP per µg DNA plasmid) can be complexed to DNA plasmid via: (1) nonspecific interactions; (2) electrostatic complexation via cationic residues on the NTP-scaffold; (3) direct chemical crosslinking of the NTP to the plasmid at ratios from 1 NTP per plasmid to >100 NTPs per plasmid; (4) co-aggregation of NTP monomers or aggregated multimers of NTP with cationic peptides or cationic polymers that condense plasmid; or (5) co-aggregation of NTP with cationic lipids containing both hydrophobic and charged moieties that facilitate the interaction of the NTP with the DNA. These complexes of the NTP and plasmid can then be delivered to cells at doses ranging from 0.01 to 100 µg of plasmid per $10^6$ cells via: (1) direct incubation; (2) scrape loading; (3) calcium phosphate precipitation; (4) electroporation; (5) radiofrequency poration; (6) microinjection; (7) ultrasound permeabilization of membrane; (8) detergent loading to transiently permeabilized membranes; (9) cold-shock loading or heat-shock loading of cells; (10) lipofection with cationic/neutral lipids combinations such as DMRIE (N-[1,(2,3)-dimyristyloxy)propyl]-N,N-dimethyl-N-(2-hydroxyethyl)ammonium bromide (DMRIE)/dioleoyl phosphatidylethanolamine (DOPE), DOSPER (1,3-dioleolyoxy-2-(6-carboxyspermyl)-propyl amine/DOPE, lipofectamine formulation (DOSPA/DOPE), lipofectin formulation (DOTMA/DOPE), or DOTAP/cholesterol; (11) lipofection with anionic lipids; (12) lipofection with neutral lipids such as DOPE or cholesterol; (13) delivery with cationic polymers such as polyethyleneimine (PEI), polyhistidine, polylysine, transferrin conjugated polylysine; receptor-targeted polylysine containing RGD sequence or antibodies against cellular receptors; (14) anionic polymers such as heparin; (15) charged proteins such as mixtures of histone isoforms or purified histone fractions; (16) endosome escape agents such as chloroquine or peptides, hydrophobic sequences of amphipathic peptides, viral subfractions that contain fusogenic activity to promote endosome escape; or (17) combinations of the above approaches.

Example 9

Intravenous Delivery of NTP or NTP-Scaffold with Plasmid to Animals

An NTP containing the M9 sequence or other nonclassical NLS (from 0.1 µg to 100 µg NTP per µg DNA plasmid) can be complexed to DNA plasmid via: (1) nonspecific interactions; (2) electrostatic complexation via cationic residues on the NTP-scaffold; (3) direct chemical crosslinking of the M9 containing NTP to the plasmid at ratios from 1 NTP per plasmid to >100 NTPs per plasmid; (4) co-aggregation of NTP monomers or aggregated multimers of NTP with cationic peptides or cationic polymers that condense plasmid; or (5) co-aggregation of NTP with cationic lipids containing both hydrophobic and charged moieties that facilitate the interaction of the NTP with the DNA. The formed complex can then be injected intravenously for delivery to the pulmonary endothelium, hepatocytes, hepatoreticuloendothelium, microvascular capillaries, arterioles, and venules. Such formulations for injection can range in dosage from 0.1 to 100 mg of plasmid. The complexes of the NTP and plasmid can be injected in combination with: saline buffer, (2) ultrasound permeabilization of tissue structures; (3) detergent loading to transiently permeabilized membranes; (4) cold-shock loading or heat-shock loading of cells; (5) lipofection with cationic/neutral lipids combinations such as DMRIE (N-[1,(2,3)-dimyristyloxy)propyl]-N,N-dimethyl-N-(2-hydroxyethyl)ammonium bromide (DMRIE)/dioleoyl phosphatidylethanolamine (DOPE), DOSPER (1,3-dioleolyoxy-2-(6-carboxyspermyl)-propyl amine/DOPE, lipofectamine formulation (DOSPA/DOPE), lipofectin formulation (DOTMA/DOPE), DOTAP/cholesterol, 3þ[N—(N',N'-(dimethylaminoethane)carbamoyl cholesterol (DC-cholesterol)/DOPE; Lysyl-phosphatidylethanoloamine (PE), DOTMA/cholesterol, or polylysine/DOPE; (6) lipofection with anionic lipids; (7) lipofection with neutral lipids such as DOPE or cholesterol; (8) delivery with cationic polymers such as polyethyleneimine (PEI), polyhistidine, polylysine, transferrin conjugated polylysine; receptor-targeted polylysine containing RGD sequence; (9) anionic polymers such as heparin; (10) or charged proteins such as mixtures of histone isoforms or purified histone fractions; (11) endosome escape agents such as chloroquine or peptides, hydrophobic sequences of amphipathic peptides, or viral subfractions that contain fusogenic activity to promote endosome escape, or (12) combinations of the above approaches.

Example 10

Intramuscular Delivery of NTP or NTP-Scaffold with Plasmid to Animals

An NTP containing the M9 sequence or other nonclassical NLS (from 0.001 µg to 100 µg NTP per µg DNA plasmid) can be complex to DNA plasmid via: (1) nonspecific interactions; (2) electrostatic complexation via cationic residues on the NTP-scaffold; (3) direct chemical crosslinking of the M9 containing NTP to the plasmid at ratios from 1 NTP per plasmid to >100 NTPs per plasmid; (4) co-aggregation of NTP monomers or aggregated multimers of NTP with cationic peptides or cationic polymers that condense plasmid; or (5) co-aggregation of NTP with cationic lipids containing both hydrophobic and charged moieties that facilitate the interaction of the NTP with the DNA such as charged anesthetics including bupivacaine-HCl. These complexes can then be injected intramuscularly for delivery to the skeletal muscle cells, and other muscle resident cells such as lymphocytes, macrophages, antigen presenting cells. Such formulations for injection can range in dosage from 0.1 to 100 mg of plasmid. These complexes of the NTP and plasmid can be injected in combination with: (1) saline buffer, (2) ultrasound permeabilization of tissue structures; (3) detergent loading to transiently permeabilized membranes; (4) cold-shock loading or heat-shock loading of cells; (5) lipofection with cationic/neutral lipids combinations such as DMRIE (N-[1,(2,3)-dimyristyloxy)propyl]-N,N-dimethyl-N-(2-hydroxyethyl)ammonium bromide (DMRIE)/dioleoyl phosphatidylethanolamine (DOPE), DOSPER (1,3-dioleolyoxy-2-(6-carboxyspermyl)-propyl amine/DOPE, lipofectamine formulation (DOSPA/DOPE), lipofectin formulation (DOTMA/DOPE), DOTAP/cholesterol, 3β[N—(N',N'-(dimethylaminoethane)carbamoyl cholesterol (DC-cholesterol)/DOPE; Lysyl-phosphatidylethanoloamine (PE), DOTMA/cholesterol; or polylysine/DOPE; (6) lipofection with anionic lipids; (7) lipofection with neutral lipids such as DOPE or cholesterol; (8) delivery with cationic polymers such as polyethyleneimine (PEI), polyhistidine, polylysine, transferrin conjugated polylysine or receptor-targeted polylysine containing RGD sequence; (9) anionic polymers such as heparin; (10) charged proteins such as mixtures of histone isoforms or purified histone fractions; (11) endosome escape peptides, hydrophobic sequences of amphipathic peptides, or viral subfractions that contain fusogenic activity to promote endosome escape; or (12) combinations of the above approaches.

Example 11

Intraluminal Delivery of NTP or NTP-scaffold with Plasmid to Animals

An NTP containing the M9 sequence or other nonclassical NLS (from 0.001 μg to 100 mg NTP per μg DNA plasmid) can be complex to DNA plasmid via: (1) nonspecific interactions; (2) electrostatic complexation via cationic residues on the NTP-scaffold; (3) direct chemical crosslinking of the M9 containing NTP to the plasmid at ratios from 1 NTP per plasmid to >100 NTPs per plasmid; (4) co-aggregation of NTP monomers or aggregated multimers of NTP with cationic peptides or cationic polymers that condense plasmid; (5) co-aggregation of NTP with cationic lipids containing both hydrophobic and charged moieties that facilitate the interaction of the NTP with the DNA; or (6) monomers for in situ polymerization to the vascular wall including light activated or free radical initiated polymerization. These complexes can then be delivered intraluminally with a single port catheter, single balloon catheter, double balloon catheter, porous balloon catheter, or ultrasound catheter for delivery to the endothelial cells or underlying smooth muscle cells, and other vessel wall resident cells such as foam cells, neutrophils, lymphocytes, macrophages, and antigen presenting cells. Such formulations for catheter delivery to the vessel can range in dosage from 0.1 to 100 mg of plasmid. These complexes of the NTP and plasmid can be perfused through the catheter to the local site of delivery in combination with: (1) saline buffer, (2) ultrasound permeabilization of vessel structures; (3) detergent loading to transiently permeabilized membranes; (4) cold-shock loading or heat-shock loading of cells; (5) lipofection with cationic/neutral lipids combinations such as DMRIE (N-[1,(2,3)-dimyristyloxy)propyl]-N, N-dimethyl-N-(2-hydroxyethyl)ammonium bromide (DMRIE)/dioleoyl phosphatidylethanolamine (DOPE), DOSPER (1,3-dioleolyoxy-2-(6-carboxyspermyl)-propyl amine/DOPE, lipofectamine formulation (DOSPA/DOPE), lipofectin formulation (DOTMA/DOPE), DOTAP/cholesterol, 3β[N—(N',N'-(dimethylaminoethane)carbamoyl cholesterol (DC-cholesterol)/DOPE; Lysyl-phosphatidylethanoloamine (PE), DOTMA/cholesterol, or polylysine/DOPE; (6) lipofection with anionic lipids; (7) lipofection with neutral lipids such as DOPE or cholesterol; (8) delivery with cationic polymers such as polyethyleneimine (PEI), polyhistidine, polylysine, transferrin conjugated polylysine or receptor-targeted polylysine containing RGD sequences or antibodies; (9) anionic polymers such as heparin; (10) charged proteins such as mixtures of histone isoforms or purified histone fractions; (11) endosome escape peptides, hydrophobic sequences of peptides, or viral subfractions that contain fusogenic activity to promote endosome escape, or (12) combinations of the above approaches.

What is claimed is:

1. A compound comprising:
   (a) a cationic peptide scaffold selected from the group of SEQ ID NO:2, SEQ ID NO:15, SEQ ID NO:16, SEQ ID NO:17, and SEQ ID NO:18; and
   (b) a nuclear targeting peptide containing a nonclassical, nuclear localization sequence of SEQ ID NO:3 or SEQ ID NO:4, said cationic peptide scaffold being conjugated to said nuclear targeting peptide via a hydrolytic-resistant chemical linkage selected from the group of: succinimidyl 4-(N-maleimidomethyl)cyclohexane-I; bis-maleimidoethane; bis-maleimidohexane; 1,4-bis-maleimidyl-2,3-dihydroxybutane; 1,4-bis-maleimidobutane; N-succinimidyl[4-iodoacetyl]aminobenzoate; N-succinimidyl iodoacetate; succinimidyl 3-[bromoacetamido]propionate; succinimidyl 4-[p-maleimidophenyl] butyrate; succinimidyl-6-[(β-maleimidopropionamido) hexanoate]; N-succinimidyl 3-[2-pyridyldithio] propionate; N-[γ-maleimidobutyryloxy] sulfosuccinimide ester; N-[κ-maleimidoundecanoyloxy]-sulfosuccinimide ester; m-maleimidobenzoyl-N-hydroxysulfosuccinimide ester; and N-succinimidyl-[4-vinylsulfonyl]benzoate.

2. A composition comprising the compound of claim 1 and a plasmid containing a selected nucleic acid sequence.

3. The composition of claim 2 wherein the peptide scaffold is conjugated to the nuclear targeting peptide and a complex is formed between the plasmid and the conjugate.

4. A method for expressing a selected nucleic acid sequence in eukaryotic cells comprising contacting cells with a mixture of a selected nucleic acid sequence and a compound of claim 1.

5. A method for expressing a selected nucleic acid sequence in eukaryotic cells comprising forming a complex between a plasmid containing the selected nucleic acid sequence and a compound of claim 1; and contacting cells with the complex.

6. Eukaryotic cells transfected with a complex comprising a plasmid containing a selected nucleic acid sequence and a compound of claim 1.

* * * * *